United States Patent [19]
Bottaro et al.

[11] Patent Number: 5,889,161
[45] Date of Patent: Mar. 30, 1999

[54] N,N'-AZOBIS-NITROAZOLES AND ANALOGS THEREOF AS IGNITER COMPOUNDS FOR USE IN ENERGETIC COMPOSITIONS

[75] Inventors: Jeffrey C. Bottaro, Mountain View; Robert J. Schmitt; Paul E. Penwell, both of Palo Alto, all of Calif.

[73] Assignee: SRI International, Menlo Park, Calif.

[21] Appl. No.: 78,302

[22] Filed: May 13, 1998

[51] Int. Cl.⁶ .................. C07D 403/12; C07D 487/12; C07D 207/50
[52] U.S. Cl. .............. 534/551; 149/55; 149/56; 149/88; 149/109.6
[58] Field of Search ................................. 534/551

[56] References Cited

U.S. PATENT DOCUMENTS

| | | | |
|---|---|---|---|
| 2,021,478 | 11/1935 | Brun et al. | 534/551 |
| 2,090,745 | 8/1937 | Brun et al. | 534/551 |
| 3,773,746 | 11/1973 | Jack et al. | 534/551 |
| 4,623,409 | 11/1986 | Lee | 149/92 |
| 5,035,757 | 7/1991 | Poole | 149/46 |
| 5,348,122 | 9/1994 | Vanmaele | 534/551 |
| 5,386,775 | 2/1995 | Poole et al. | 102/289 |
| 5,472,647 | 12/1995 | Blau et al. | 264/3.1 |
| 5,501,823 | 3/1996 | Lund et al. | 264/3.1 |
| 5,531,941 | 7/1996 | Poole | 264/304 |
| 5,661,261 | 8/1997 | Ramaswamy et al. | 149/36 |

FOREIGN PATENT DOCUMENTS

95/00462  1/1995  WIPO.

OTHER PUBLICATIONS

Anderson et al., J. Chem. Soc. Perkin Trans. II, 1989, 12, 2055–2058.
Glover et al., J. Chem. Soc. Perkin Trans I, 1974, 15, 1792–1794.
Neunhoeffer et al., Liebigs Ann. Chem., 1985, 9, 1732–1751.
Ohsawa et al., J. Org. Chem., 1985, 50(26), 5520–5523.
Semenov et al., Chemical Abstracts, 118:80874f, 1993.
Moriarty et al., Chemical Abstracts, 114:23470, 1991.
Lee, "Synthesis of 1,1'–Dinitro–3,3'–Azo–1,2,4–Triazole," Los Alamos National Laboratory Publication No. LA–10346–MS, DE85 013937 (1985).

*Primary Examiner*—Fiona T. Powers
*Attorney, Agent, or Firm*—Dianne E. Reed; Bozicevic & Reed LLP

[57] ABSTRACT

Novel energetic compounds are provided comprising N,N'-azobis-nitroazoles or analogs thereof. The compounds are useful as igniter materials in a variety of energetic compositions, particularly gas-generating compositions for inflating automobile or aircraft occupant restraint devices. The compounds are also useful in solid rocket propellant compositions, and as primary explosives to be used as detonators, blasting caps, firearms, and the like. Methods for synthesizing the compounds and manufacturing energetic compositions herewith are provided as well.

18 Claims, No Drawings

N,N'-AZOBIS-NITROAZOLES AND ANALOGS THEREOF AS IGNITER COMPOUNDS FOR USE IN ENERGETIC COMPOSITIONS

REFERENCE TO GOVERNMENT SUPPORT

This invention was funded in part by the United States Office of Naval Research under Contract No. N00014-95-C-0209. The United States Government has certain rights in this invention.

TECHNICAL FIELD

The present invention relates generally to energetic compositions and components thereof More particularly, the invention relates to novel igniter compounds useful in energetic compositions, to energetic compositions containing the novel compounds, and to methods of synthesis and manufacture. A primary use of the novel compounds is in gas generating compositions for inflating automotive and aircraft occupant restraint devices.

BACKGROUND

"Energetic" compounds are used extensively in a wide variety of applications, e.g., in rocket propellants, explosive formulations, and the like. It is generally preferred that such materials have a high energy content yet be relatively insensitive to impact, such that accidents are avoided and energy is released only when intended. The requirements of insensitivity and high energy are in conflict, making the development of new energetic materials a difficult and challenging synthetic problem.

In developing new energetic compounds, a number of factors come into play. For example, heats of formation, density, melting and decomposition temperatures, carbon content and, generally, nitrogen content, are properties which must be considered. Energetic compounds should display good thermal and shock properties, have high heats of formation, and be straightforward to synthesize in bulk. It is generally preferred that an energetic compound have a melting point above about 100° C., an exothermic heat of combustion, and a high decomposition temperature, with a relatively large separation between melting point and decomposition temperature preferred such that an energetic composition may be melt cast from the selected compound.

A number of energetic compounds are known as useful in the manufacture of oxidizers, explosives and the like. Energetic compounds have also been disclosed as useful to inflate automobile and aircraft occupant restraint bags. However, previously known materials are generally limited in one or more ways, e.g., they are overly impact-sensitive, difficult to synthesize on a large scale, not sufficiently energetic, or the like. In addition, energetic compositions used to inflate occupant restraint bags in automobiles and aircraft typically contain potentially toxic heavy metal igniter materials, e.g., mercury compounds, $Pb(N_3)_2$ or the like.

The present invention provides a new class of compounds which overcomes the aforementioned limitations in the art. The energetic compounds to which the invention pertains are commonly referred to as "igniter materials" or "igniter compounds," i.e., compounds which act as primary explosives in an energetic composition. Igniter compounds should be thermally stable, typically up to a temperature of at least about 150° C.; ideally, the compounds should also have a relatively high heat of formation, and be safe, economical and straightforward to synthesize in relatively high yield. The compounds now provided herein meet all of these criteria, and outperform conventional igniters such as lead azide and lead styphnate. In addition, it is important to note that the present compounds are thermally stable as well as shock-sensitive; normally, such compounds are either thermally stable or shock-sensitive, but not both.

The following references relate to one or more aspects of the present invention, and as such may provide background information not explicitly included herein. For example, U.S. Pat. No. 4,623,409 to Lee describes 1,1'-dinitro-3,3'-azo-1,2,4-triazole, a compound having the structure

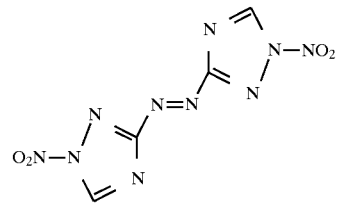

and stated to be useful as an explosive agent and as a candidate for use in high-energy propellant applications. The compound is synthesized by oxidizing 3-amino-1,2,4-triazole with potassium permanganate, followed by nitration of the intermediate so formed. U.S. Pat. No. 5,472,647 to Blau et al. describes substituted tetrazoles as gas generants. Examples of the tetrazoles are bicyclic compounds having the structure

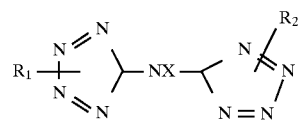

in which X, $R_1$ and $R_2$ represent H, methyl, ethyl, cyano, nitro, amino, tetrazolyl, a metal, or a nonmetallic cation of a nitrogen-containing base. Other references of interest include U.S. Pat. No. 5,501,823 to Lund et al. and U.S. Pat. No. 5,661,261 to Ramaswamy et al., which pertain to gas generating compositions, and U.S. Pat. Nos. 5,035,757 to Poole and 5,531,941 to Poole et al., which describe compositions for inflating automobile airbags. The latter compositions may contain nitrated tetrazoles; Poole et al. '775 mentions 5-nitrotetrazole and 5-nitroaminotetrazole, while Poole '757 mentions 3-nitro-1,2,4-triazole-5-one. Both patents disclose the use of metal salts such as strontium nitrate.

SUMMARY OF THE INVENTION

It is accordingly a primary object of the invention to address the above-mentioned need in the art by providing novel compounds useful as igniter materials in energetic compositions.

It is another object of the invention to provide such compounds in the form of N,N'-azobis-nitroazoles and analogs thereof.

It is a further object of the invention to provide energetic compositions containing such a compound as an igniter material.

It is yet a further object of the invention to provide such energetic compositions in the form of gas-generating compositions for inflating automotive and aircraft occupant restraint bags.

It is still a further object of the invention to provide such energetic compositions in the form of solid rocket propellant formulations, explosive compositions, and the like.

It is still a further object of the invention to provide a method for synthesizing the novel compounds.

Additional objects, advantages and novel features of the invention will be set forth in part in the description which follows, and in part will become apparent to those skilled in the art upon examination of the following, or may be learned by practice of the invention.

In a first embodiment, the invention relates to novel compounds useful as energetic materials. The compounds have the structural formula (I)

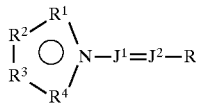

wherein:

$R^1$, $R^2$, $R^3$ and $R^4$ are independently selected from the group consisting of N, N→O, (N$^+$—R$^a$)Z$^-$, CH, C—R$^b$, C—NR$^c$R$^d$, and C—NO$_2$ in which R$^a$ and R$^b$ are independently $C_1$–$C_{24}$ alkyl or fluoro, R$^c$ and R$^d$ are independently H or $C_1$–$C_{24}$ alkyl, and Z$^-$ is a counterion, or wherein $R^4$ may be a nitrogen atom or carbon atom linked to an atom contained within the molecular moiety R at a position that is beta to J$^2$; and $J^1$ and $J^2$ are independently either N or N→O, with the proviso that $J^1$ and $J^2$ are not both N→O.

Particularly preferred compounds are wherein two five-membered nitrogen-containing heterocycles, e.g., triazoles or tetrazoles, are linked to each other through an azo bond. The heterocycles preferably contain at least one nitro substituent bound to a ring carbon atom.

In another embodiment of the invention, energetic compositions are provided containing one or more of the novel compounds as igniter materials. These energetic compositions may take any number of forms and have a variety of uses, as the present compounds are ideal primary explosives to be used as detonators, in blasting caps, and the like. In addition, the compounds of the invention are useful as igniter materials to be incorporated into energetic, gas-generating compositions for inflating automotive or aircraft occupant restraint devices. As will be appreciated by those skilled in the art, the aforementioned uses are exemplary in nature and not intended to represent a comprehensive list of possibilities; that is, in general, the novel compounds may be used in any energetic composition wherein an igniter material is necessary.

DETAILED DESCRIPTION OF THE INVENTION

Definitions and nomenclature:

Before the present compounds, compositions and methods are disclosed and described, it is to be understood that this invention is not limited to specific molecular structures, ligands, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an igniter compound" or "an igniter" in a composition means that more than one such compound can be present in the composition. Similarly, reference to "a nitro group" as in a compound substituted with "a nitro group" includes the possibility of substitution with more than one nitro group, reference to "a substituent" includes one or more substituents, and the like.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "aryl" as used herein refers to an aromatic species containing 1 to 5 aromatic rings, either fused or linked, and either unsubstituted or substituted with 1 or more substituents typically selected from the group consisting of lower alkyl, halogen, —NH2 and —NO$_2$. Preferred aryl substituents contain 1 to 3 fused or linked aromatic rings, and particularly preferred aryl substituents contain 1 aromatic ring or 2 fused or linked aromatic rings.

The term "heterocyclic" refers to a five- or six-membered monocyclic structure or to an eight- to eleven-membered bicyclic heterocycle. Generally, although not necessarily, the heterocyclic substituents herein are aromatic. Each heterocycle consists of carbon atoms and from one to four heteroatoms selected from the group consisting of nitrogen, oxygen and sulfur. typically nitrogen. As used herein, the terms "nitrogen heteroatoms" and "sulfur heteroatoms" include any oxidized form of nitrogen and sulfur. Preferred heterocyclic groups are five-membered rings containing one to four nitrogen atoms, and thus include pyrrole, pyrazole, imidazole, 1,2,3-triazole, 1,2,4-triazole and tetrazole, with 1,2,4-triazole and tetrazole particularly preferred.

"Halo" or "halogen" refers to fluoro, chloro, bromo or iodo, and usually relates to halo substitution for a hydrogen atom in an organic compound. Of the halos, chloro and fluoro are generally preferred, with fluoro particularly preferred.

"Optionally" or "optionally" means that the subsequently described event or circumstance may or may not occur, and that the description includes instances where said event or circumstance occurs and instances where it does not. For example, the phrase "optionally substituted" aromatic ring means that the aromatic ring may or may not be substituted and that the description includes both an unsubstituted aromatic ring and an aromatic ring bearing one or more substituents.

The term "energetic" to describe the various compounds disclosed and claimed herein is used to refer to a material having a high energy content as represented by an exothermic (negative) heat of combustion.

The Novel Compounds:

The energetic compounds of the invention are represented by structural formula (I)

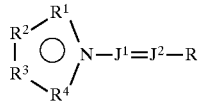

wherein R, $R^1$, $R^2$, $R^3$, $R^4$, $J^1$ and $J^2$ are as defined earlier herein.

That is, R is a monocyclic or bicyclic aromatic substituent. If monocyclic, R is either a five-membered or six-membered ring, and may or may not be a heterocycle. If R is heterocyclic, the heterocyclic ring contains one to four nitrogen atoms.

$R^1$, $R^2$, $R^3$ and $R^4$ are independently selected from the group consisting of N, N→O, (N$^+$—R$^2$)Z$^-$, CH, C—R$^b$, C—NR$^c$R$^d$, and C—NO$_2$ in which R$^a$ and R$^b$ are independently $C_1$–$C_{24}$ alkyl or fluoro, R$^c$ and R$^d$ are independently H or $C_1$–$C_{24}$ alkyl, and Z$^-$ is a counterion. Preferably, R$^a$ and $R^b$ are lower alkyl, and $R^c$ and $R^d$ are independently either H or lower alkyl. However, particularly preferred $R^1$, $R^2$, $R^3$ and $R^4$ groups are N, CH and C—$NO_2$. Alternatively, $R^4$ may be a nitrogen atom or carbon atom linked to an atom contained within the molecular moiety R at a position beta to $J^2$. $Z^-$ may be any suitable counterion that does not interfere with the utility or stability of the compounds. Examples of suitable counterions include, but are not limited to, anions of inorganic and organic acids, e.g., $NO_3^-$, $NO_2^-$, $N(NO_2)_2^-$, $ClO_4^-$ and $C(NO_2^-)_3^-$, halogen anions, particularly $F^-$, and heterocyclic anions such as the anion of 3,5-dinitro-1,2,4-triazole.

$J^1$ and $J^2$ are either N or N→O, with the proviso that $J^1$ and $J^2$ are not both N→O. In a preferred embodiment, both $J^1$ and $J^2$ are N, such that the linkage between the nitrogen-containing heterocycle and the R substituent is an azo bond.

One group of compounds in which R is a monoheterocycle is represented by structural formula (II)

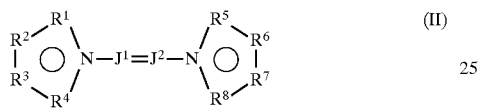

in which $R^5$, $R^6$, $R^7$ and $R^8$ are independently selected from the group consisting of N, N→O, $(N^+—R^a)Z^-$, CH, C—$R^b$, C—$NR^cR^d$, and C—$NO_2$, and $J^1$, $J^2$, $R^a$, $R^b$, $R^c$ and $R^d$ are as defined earlier herein, or wherein $R^8$ is a carbon atom or a nitrogen atom bound to a carbon atom or a nitrogen atom at $R^4$ so as to form a fused three-ring structure. Preferred $R^5$ through $R^8$ groups are N, CH and C—$NO_2$. Specific compounds encompassed by structure (II) include, but are not limited to, the following:

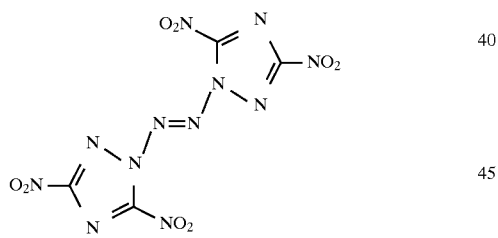

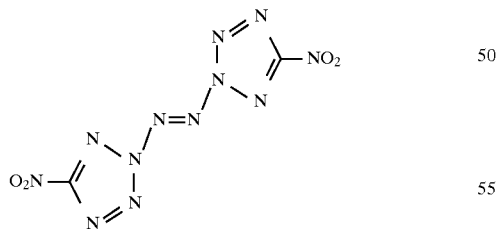

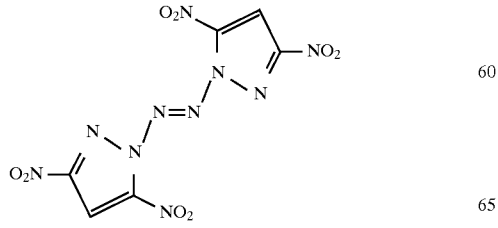

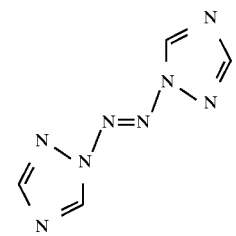

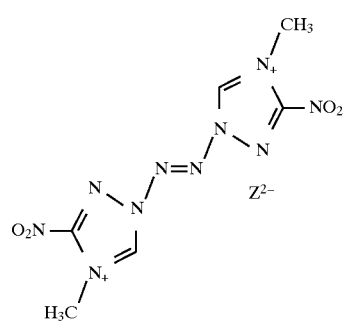

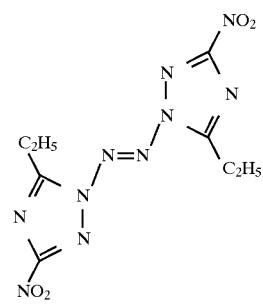

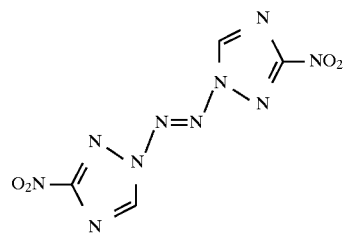

Examples of compounds wherein $R^4$ and $R^8$ are linked include, but are not limited to, the following:

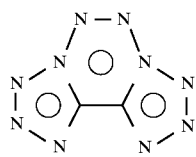

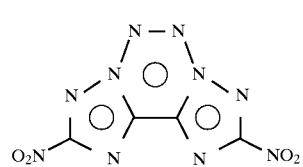

-continued

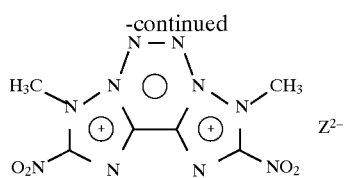

Another class of compounds is represented by formula (III):

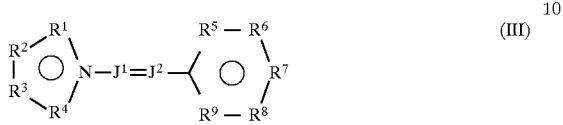

wherein $J^1$, $J^2$, $R^1$, $R^2$, $R^3$, $R^4$, $R^5$, $R^6$, $R^7$ and $R^8$ are as defined previously, and wherein $R^9$ is defined as for $R^1$ through $R^8$. Specific compounds encompassed by structure (III) include, but are not limited to, the following:

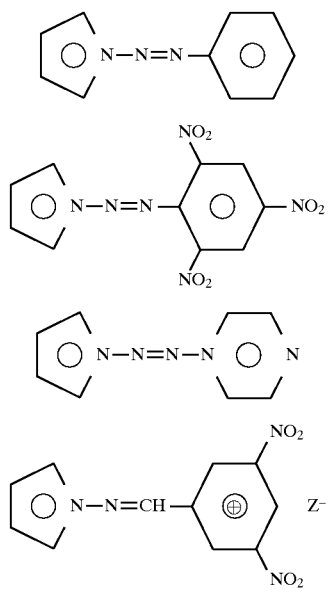

When R is a bicyclic substituent, the individual cyclic structures may be fused or linked, and may or may not be heterocyclic. Preferably, however, when R is bicyclic, the substituent comprises two fused five- or six-membered nitrogen-containing heterocycles or two five-membered nitrogen-containing heterocycles joined through an azo linkage. The latter compounds include, but are not limited to, those defined by structure (IV) and (V)

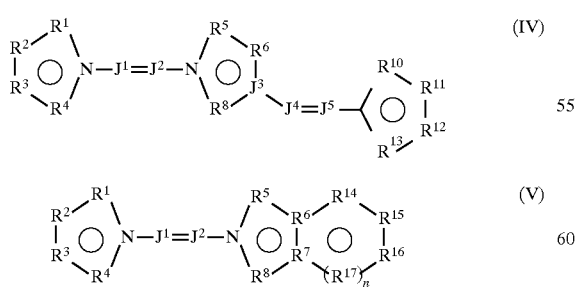

wherein $J^3$ is C, $J^4$ and $J^5$ are independently N or N→O, with the proviso that $J^4$ and $J^5$ are not both N→O, and $R^1$ through $R_8$ and $R_{10}$ through $R^{17}$ are independently selected from the group consisting of N, N→O, $(N^+\!\!-\!\!R^a)Z^-$, CH, C—$R^b$, C—$NR^cR^d$, and C—$NO_2$ in which $R^a$ and $R^b$ are independently $C^1$–$C_{24}$ alkyl or fluoro, $R^c$ and $R^d$ are independently H or $C_1$–$C_{24}$ alkyl, and $Z^-$ is a counterion. The integer "n" is 0 or 1. Preferably, n is 0, $R^a$ and $R^b$ are lower alkyl, and $R^c$ and $R^d$ are H or lower alkyl. Specific compounds encompassed by structure (IV) include, but are not limited to, the following:

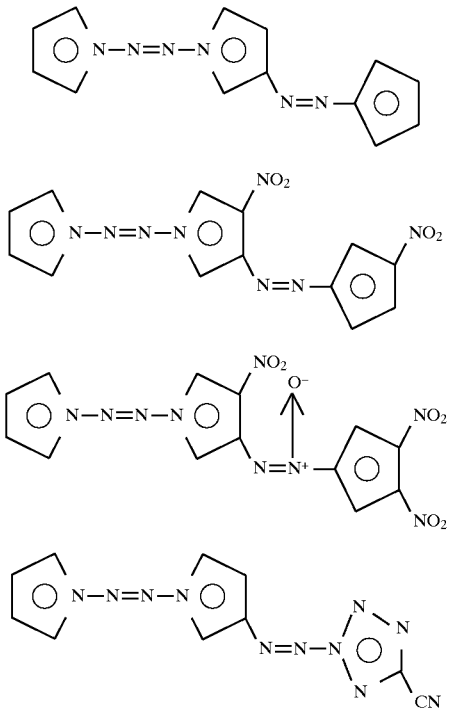

Specific compounds encompassed by structure (V) include, but are not limited to, the following:

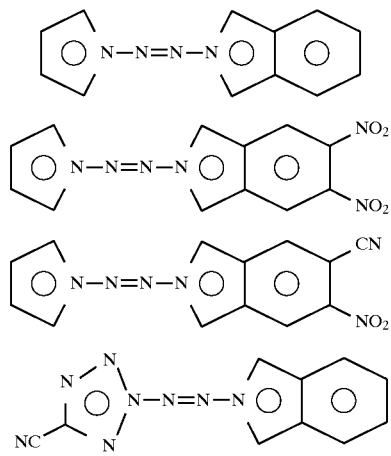

Energetic Compositions:

As will be appreciated by those skilled in the art, the compounds of the invention may be used as igniter materials in a variety of energetic compositions. A primary area of interest is in gas-generating compositions, e.g., for inflating automotive and aircraft occupant restraint devices. Current commercially used gas-generating compositions for inflating such devices involve the use of heavy metal igniter compounds; the present invention avoids the need for heavy metals. That is, upon oxidation, the compounds of the invention give rise to products containing only nitrogen, carbon, oxygen and hydrogen, and possibly fluorine if the igniter contains a fluoro substituent in its molecular structure.

Gas-generating compositions for inflating airbags or for other uses contain a compound of the invention as discussed earlier herein, a propellant composition or "secondary" explosive, and, optionally, an oxidizer. Secondary explosives are high explosives that are more difficult to detonate than primary explosives. Typically, igniter materials, or primary explosives, are used to ignite secondary explosives. Secondary explosives differ from primary explosives in three ways: they do not easily go from burning to detonation, require larger shocks to ignite and are more difficult to ignite using electrostatic ignition. Examples of secondary explosives include 2,4,6-trinitrotoluene (TNT), cyclo-1,3,5-trimethylene-2,4,6-trinitramine (RDX or cyclonite), high melting explosives (HMX), picric acid, and the like. Any suitable oxidizer may be used, as will be appreciated by those skilled in the art. Examples of oxidizers that may be incorporated into the present gas-generating compositions include, but are not limited to, ammonium nitrate (AN), phase-stabilized ammonium nitrate (PSAN), ammonium dinitramide (ADN), potassium nitrate (KN), potassium dinitramide (KDN), sodium peroxide ($Na_2O_2$), ammonium perchlorate (AP), and KDN-AN, a cocrystallized form of potassium dinitramide and ammonium nitrate.

The aforementioned gas-generating compositions may also, if desired, contain a gas-generating fuel and a binder. Suitable gas-generating fuels include triaminoguanidine nitrate (TAGN), diaminoguanidine nitrate (DAGN), monoaminoguanidine nitrate (MAGN), 3-nitro-1,2,4-triazole-5-one (NTO), salts of NTO, urazole, triazoles, tetrazoles, guanidine nitrate, oxamide, oxalyldihydrazide, melamine, various pyrimidines, semicarbazide ($H_2N$—(CO)—$NHNH_2$), azodicarbonamide ($H_2N$—(CO)—N=N—(CO)—$NH_2$), and mixtures thereof Suitable binders are generally organic polymeric materials, e.g., polycarbonates, polyesters, polyurethanes and the like.

Another area of interest is in the manufacture of solid rocket propellant compositions. Such compositions will contain, in addition to the igniter material, a binder composition and fuel. Examples of binder materials for use in propellant applications include but are not limited to polyoxetanes, polyglycidyl azide, hydroxyl-terminated polybutadiene, polybutadiene-acrylonitrileacrylic acid terpolymer, polyethers, polyglycidyl nitrate, and polycaprolactone; see, e.g., U.S. Pat. No. 5,292,387 to Highsmith et al. Suitable propellant fuels will generally be metallic, e.g., aluminum, beryllium, boron, magnesium, zirconium, or mixtures or alloys thereof. Other components for incorporation into propellant compositions include plasticizers, burn rate modifiers, ballistic additives, and the like.

The compounds of the invention are useful in a number of other contexts as well. For example, the high thermal stability and high impact stability of the novel compounds render them ideal primary explosives to be used as detonators, in blasting caps, firearms, and the like. In any of these compositions, it is of course necessary to maintain separation between the igniter material and the remainder of the composition, i.e. the secondary explosive, until detonation is desired.

Synthesis and Manufacture:

The compounds of the invention may be readily synthesized in a variety of ways using techniques that are relatively straightforward and readily scaled up. This is in contrast to prior synthetic methods used to make energetic nitrogen-containing heterocyclic compounds such as ANTA, which although having a reasonable heat of formation and the desired impact sensitivity, is not straightforward to synthesize nor readily made in bulk.

Synthesis of the present compounds will generally involve a starting material which is a N-amino nitroazole, e.g., an N-amino triazole or tetrazole. The preferred reaction involves the buffered hypochlorite oxidation of the starting material, resulting in an azo linkage joining the two azole rings. Other compounds of the invention may be made using an analogous reaction and similar starting materials, substituted as desired.

Synthetic details not explicitly disclosed herein will be within the knowledge of or may readily deduced by those skilled in the art of synthetic organic chemistry, or may be found in the relevant texts such as Kirk-Othmer's *Encyclopedia of Chemical Technology*, House's *Modern Synthetic Reactions*, C. S. Marvel and G. S. Hiers' text, *ORGANIC SYNTHESIS*, Collective Volume 1, or in T. L. Gilchrist, *Heterocyclic Chemistry*, 2nd Ed. (New York: John Wiley & Sons, 1992) or the like. Synthesis of representative compounds is exemplified below.

Manufacture of the gas-generating and/or propellant compositions may be carried out using conventional means, as will be appreciated by those skilled in the art. A suitable method for preparing anhydrous gas-generating composition is disclosed, for example, in U.S. Pat. No. 5,473,647 to Blau et al. and in international patent publication WO 95/00462 (Poole et al.). Typically, a tetrazole or bitetrazoleamine, such as bis(1(2)H-tetrazol-5-yl)-amine (BTA) monohydrate is blended with an oxidizer such as copper oxide and mixed with water to create a paste. The paste is treated with calcium stearate and then dried to yield anhydrous particles that can be shaped into any desired shape. In the Poole et al. method, the gas-generating composition is prepared by dry blending guanidine nitrate, strontium nitrate, bentonite clay and the potassium salt of 5-aminotetrazole, and then forming pellets by compression molding. Of course, other methods for manufacture may be used as well. Such methods are described in the pertinent literature or will be known to those familiar with the preparation of energetic compositions.

EXPERIMENTAL

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

EXAMPLE 1

Synthesis of 1,1'-Azobis-(3-Nitro-1,2,4-triazole):

1-Amino-3-nitro-1,2,4-triazole (1.3 g, 10 mmol) was dissolved in 10 mL of dry acetonitrile, cooled to 0° C. with stirring under argon, and treated with t-butyl hypochlorite (1.1 g, 10 mmol) over 10 minutes. The resulting solution was stirred for 24 h, at room temperature, concentrated in vacuo, and triturated with isopropyl alcohol (3 mL). The undissolved solid was collected by filtration to give 400 mg (30%) of 1,1'-azobis-(3-nitro-1,2,4-triazole). The identity of the product was confirmed using NMR spectroscopy and X-ray diffraction.

EXAMPLE 2

Synthesis of 1,1'-Azobis-(3,5-Dinitro-1,2,4-triazole):

The procedure of Example 1 may be repeated using 1-amino-3,5-dinitro-1,2,4-triazole as a starting material to prepare 1,1'-azobis-(3,5-dinitro-1,2,4-triazole).

EXAMPLE 3

Synthesis of 1,1'-Azobis-1,2,4-triazole:

The procedure of Example 1 may be repeated using 1-amino-1,2,4-triazole as a starting material to prepare 1,1'-azobis-1,2,4-triazole.

EXAMPLE 4

Synthesis of 1,1'-Azobis-(3-Nitro-1,2,4-tetrazole):

The procedure of Example 1 may be repeated using 1-amino-3-nitro-1,2,4,5-tetrazole as a starting material, to prepare 1,1'-azobis-(3-nitro-1,2,4,5-tetrazole).

EXAMPLE 5

Synthesis of 1-Azobenzenepyrrole (III):

Pyrrole (0.67 g, 10 mmol) was dissolved in 20 ml of dry THF, cooled to −5° C. with stirring under argon, and treated with t-butyllithium (0.64 g, 10 mmol). The resulting solution was stirred for 10 min., and then diazobenzene chloride (1.41 g, 10 mmol) was added. The resulting solution was stirred for 24 h at room temperature, concentrated in vacuo, and triturated with isopropyl alcohol (3 mL). The undissolved solid was collected by filtration, and separated by silica gel chromatography to give 1-azobenzenepyrrole in approximately 12% yield. The identity of the product was established using NMR and FTIR.

EXAMPLE 6

Synthesis of 1,1'-azo-(2,4,6-trinitrophenyl) pyrrole:

The procedure of Example 5 may be repeated using 1-diazo-2,4,6-trinitrophenyl chloride as a starting material, to prepare 1,1'-azo-(2,4,6-trinitrophenyl)pyrrole.

EXAMPLE 7

Synthesis of 4,1'-azo-pyridine pyrrole:

The procedure of Example 5 may be repeated using 4-diazopyridinium chloride as a starting material to prepare 4,1'-azo-pyridine pyrrole.

EXAMPLE 8

Synthesis of N-1-pyrrole-3,5-dinitrobenzylimine:

1-pyrrole amine (0.82 g, 10 mmol), 3,5-dinitrobenzaldehyde (2 g, 10 mmol), and potassium bicarbonate (5 g, 50 mmol) are stirred in dry DMF overnight. The resultant solution is concentrated in vacuo, and triturated with isopropyl alcohol (3 mL). The undissolved solid was collected by filtration, and separated by silica gel chromatography to give N-1-pyrrole-3,5-dinitrobenzylimine. The identity of the product was established by NMR and FTIR.

EXAMPLE 9

Preparation of Gas-Generating Compositions:

A solid composition for generating gases comprising 1,1'-azobis-(3-nitro-1,2,4-triazole) and an oxidizer chosen from ammonium nitrate (AN), ammonium perchlorate (AP), and ammonium dinitramide (ADN) is formed into a tablet. The tablet is ignited by either elevating the ambient temperature or by closing an electrical circuit.

EXAMPLE 10

Preparation of Propellant Compositions:

A solid composition for use as a propellant comprising 1,1'-azobis-(3-nitro-1,2,4-triazole) and an oxidizer chosen from ammonium nitrate (AN), ammonium perchlorate (AP), and ammonium dinitramide (ADN), a binder such as R-45M or GAP, with isocyanate curing agents is formed into a tablet. The tablet is ignited by closing an electrical circuit.

We claim:

1. A compound having the structural formula (I)

wherein:

R is a monocyclic nitrogen-containing heterocycle or a bicyclic aromatic substituent;

$R^1$, $R^2$, $R^3$ and $R^4$ are independently selected from the group consisting of N, N→O, $(N^+—R^a)Z^-$, CH, C—$R^b$, C—$NR^cR^d$, and C—$NO_2$ in which $R^a$ and $R^b$ are independently $C_1$–$C_{24}$ alkyl, or fluoro, $R^c$ and $R^d$ are independently H or $C_1$–$C_{24}$ alkyl, and $Z^-$ is a counterion, or wherein $R^4$ is bound to an atom contained within R and beta to $J^2$, with the proviso that at least one of $R^1$, $R^2$, $R^3$ and $R^4$ is C—$NO_2$; and $J^1$ and $J^2$ are independently either N or N—O, with the proviso that $J^1$ and $J^2$ are not both N→O.

2. The compound of claim 1, wherein $R^1$, $R^2$, $R^3$ and $R^4$ are independently selected from the group consisting of N, CH and C—$NO_2$.

3. The compound of claim 1, wherein $J^1$ and $J^2$ are N.

4. The compound of claim 1, wherein R is a monocyclic nitrogen-containing heterocycle.

5. The compound of claim 4, having the structural formula (II)

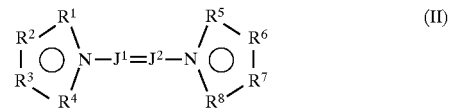

in which $R^5$, $R^6$, $R^7$ and $R^8$ are independently selected from the group consisting of N, N→O, $(N^+R^a)Z^-$, CH, C—$R^b$, C—$NR^cR^d$, and C—$NO_2$ in which $R^a$ and $R^b$ are independently $C_1$–$C_{24}$ alkyl or fluoro, and $R_c$ and $R_d$ are independently H or $C_1$–$C_{24}$ alkyl, and $Z^-$ is a counterion.

6. The compound of claim 5, wherein $R^1$, $R^2$, $R^3$, $R^4$, $R^5$, $R^6$, $R^7$ and $R^8$ are independently selected from the group consisting of N, CH and C—$NO_2$.

7. The compound of claim 6, having the structural formula

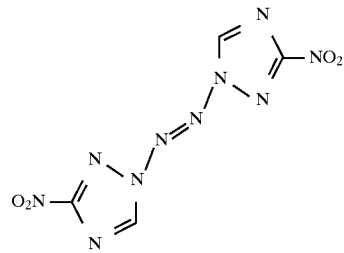

8. The compound of claim 6, having the structural formula

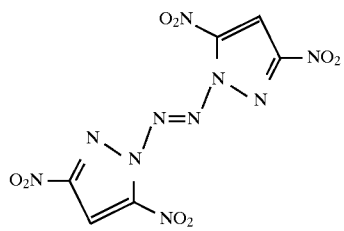

9. The compound of claim 4, having the structural formula (III)

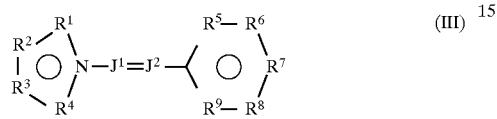

in which $R^5$, $R^6$, $R^7$, $R^8$, and $R^9$ are independently selected from the group consisting of N, N→O, $(N^+R^a)Z^-$, CH, C—$R^b$, C—$NR^cR^d$, and C—$NO_2$ in which $R^a$ and $R^b$ are independently $C_1$–$C_{24}$ alkyl or fluoro, and $R_c$ and $R_d$ are independently H or $C_1$–$C_{24}$ alkyl, and $Z^-$ is a counterion, with the proviso that at least one of $R^5$, $R^6$, $R^7$, $R^8$, and $R^9$ is N, N→O or $(N^+R^a)Z^-$.

10. The compound of claim 9, wherein $R^1$ through $R^9$ are independently selected from the group consisting of N, CH and C—$NO_2$.

11. The compound of claim 1, wherein R is a bicyclic aromatic substituent.

12. The compound of claim 11, wherein the bicyclic aromatic substituent comprises two fused aromatic rings which may or may not be heterocyclic.

13. The compound of claim 12, having the structural formula (V)

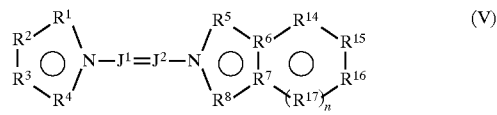

wherein $R^1$ through $R^8$ and $R^{14}$ through $R^{17}$ are independently selected from the group consisting of N, N→O, $(N^+$—$R^a)Z^-$, CH, C—$R^b$, C—$NR^cR^d$, and C—$NO_2$ in which $R^a$ and $R^b$ are independently $C_1$–$C_{24}$ alkyl or fluoro, $R^c$ and $R^d$ are independently H or $C_1$–$C_{24}$ alkyl, n is 0 or 1, and $Z^-$ is a counterion.

14. The compound of claim 11, wherein the bicyclic aromatic substituent comprises two five-membered nitrogen-containing heterocycles joined through an azo linkage.

15. The compound of claim 14, having the structural formula (IV)

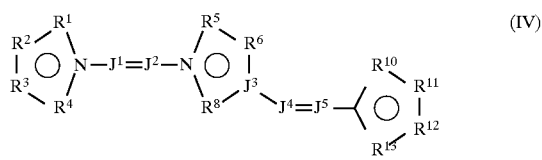

wherein $J^3$ is C, $J^4$ and $J^5$ are independently N or N→O, with the proviso that $J^4$ and $J^5$ are not both N→O, and $R^5$, $R^6$, $R^8$, $R^{10}$, $R^{11}$, $R^{12}$, and $R^{13}$ are independently selected from the group consisting of N, N→O, $N^+$—$R^a$, CH, C—$R^b$, C—$NR^cR^d$, and C—$NO_2$ in which $R^a$ and $R^b$ are independently $C_1$–$C_{24}$ alkyl, and $R^c$ and $R^d$ are independently H or $C_1$–$C_{24}$ alkyl.

16. The compound of claim 15, wherein $J^4$ and $J^5$ are both N.

17. The compound of claim 16, wherein $R^1$, $R^2$, $R^3$, $R^4$, $R^5$, $R^6$, $R^8$, $R^9$, $R^{10}$, $R^{11}$, $R^{12}$, and $R^{13}$ are independently selected from the group consisting of N, CH and C—$NO_2$.

18. The compound of claim 3, wherein one of $R^1$ and $R^2$ is N and the substituent R contains two adjacent nitrogen atoms, one of which is directly bound to $J^2$.

* * * * *